United States Patent [19]

Fravel et al.

[11] 4,153,059
[45] May 8, 1979

[54] URINARY INCONTINENCE STIMULATOR SYSTEM

[75] Inventors: Ralph P. Fravel; Ciril J. Godec, both of Saint Paul, Minn.

[73] Assignee: Minnesota Mining and Manufacturing Company, Saint Paul, Minn.

[21] Appl. No.: 844,966

[22] Filed: Oct. 25, 1977

[51] Int. Cl.² .............................................. A61N 1/36
[52] U.S. Cl. .................................................... 128/422
[58] Field of Search .............. 128/421, 422, 404, 407, 128/408, 410, 411, 419 R, 420 R, 423

[56] References Cited

U.S. PATENT DOCUMENTS

| | | | |
|---|---|---|---|
| 2,350,797 | 6/1944 | Morland et al. | 128/421 X |
| 2,700,975 | 2/1955 | Hopfinger et al. | 128/421 |
| 3,749,100 | 7/1973 | Mosel | 128/407 |
| 3,794,022 | 2/1974 | Nawracaj | 128/422 |
| 3,810,457 | 5/1974 | Bottcher et al. | 128/421 X |
| 3,851,651 | 12/1974 | Icenbice, Jr. | 128/422 |
| 3,933,147 | 1/1976 | DuVall et al. | 128/408 X |
| 3,943,938 | 3/1976 | Wexler et al. | 128/407 |
| 3,983,881 | 10/1976 | Wickham | 128/421 |

Primary Examiner—Lee S. Cohen
Attorney, Agent, or Firm—Cruzan Alexander; Donald M. Sell; Robert L. Marben

[57] ABSTRACT

A urinary incontinence stimulator system using an intra-anal electrode which provides a recurring series of pulses of varying duration and frequency to the electrode with each of such series of pulses spaced from the succeeding series by a rest period when no pulses are provided to the electrode.

9 Claims, 2 Drawing Figures

URINARY INCONTINENCE STIMULATOR SYSTEM

BACKGROUND OF THE INVENTION

1. Field of the Invention

The invention presented herein relates to urinary control using in intra-anal plug electrode assembly for applying a neuromuscular stimulating signal from a battery-powered electronic circuit to the anal sphincter of the user for causing reduction of urinary incontinence.

2. Description of the Prior Art

B. R. Hopkinson and R. Lightwood of England have reported the use of an intra-anal plug electrode assembly constructed of electrically insulative material having a central constricted portion. When positioned to extend above and below the physiological anal sphincter, the constricted portion allowed the assembly to be held in place by closure of the anal sphincter muscle. The plug had circumferential ring electrodes laterally displaced in both directions from the central constricted portion which were connected to a portable battery-operated generator capable of delivering 25 microsecond pulses at a frequency of about 30 Hz. from 0 to 20 volts. The pulses stimulated the sphincter causing it to close. The device was used to treat persons with anal incontinence, urinary incontinence or both. U.S. Pat. No. 3,749,100 to H.A. von der Mosel, indicates the method of choice for functional electrical stimulation (FES) of the sphincter using an intra-anal electrode unit is a square wave having a peak potential not greater than about 10 volts (preferably between 1 and 2 volts) and a frequency in the range from 18 to 90 Hz. The patent indicates that provision was made for adjustment of the load current by the user.

Cardiac Recorders, Ltd., has provided a system for FES using an intra-anal electrode unit which delivers 1 millisecond pulses at a rate of 200 per second with the output controlled by the user allowing the output to be increased gradually when the unit is turned on.

The nature of an FES signal provided by the prior art devices results in a phenomenon known as fatigue and habituation resulting in a decreasing response to such an FES signal. While that FES signal may be effective initially, its effectiveness diminishes quickly with time.

SUMMARY OF THE INVENTION

The fatigue and habituation problem presented by known systems providing FES of the sphincter using an intra-anal electrode unit is minimized by this invention, which provides for automatic changes in the duration and frequency of the pulses in a pseudo-random fashion with provision made for a relaxation or rest period when no pulses are supplied to the electrode unit. In one embodiment, a urinary incontinence stimulator system of this invention uses an intra-anal electrode and includes a generator means providing a series of pulses of varying duration and frequency plus an enabling means for providing a recurring enabling signal with an output circuitry connected to receive the pulses from the generator means and the enabling signals from the enabling means to provide a pulse to the intra-anal electrode for each pulse received from the generator means for a time determined by the enabling signal. The time periods between the enabling signals provides the rest period when no pulses are applied to the intra-anal electrode.

BRIEF DESCRIPTION OF THE DRAWINGS

The invention will be better understood and its various advantages will become apparent from the following description given in conjunction with the accompanying drawings in which an embodiment of the invention is illustrated by way of example and wherein.

DESCRIPTION

Figure 1:
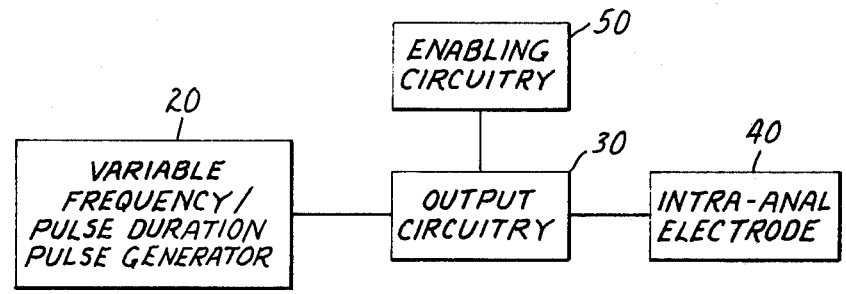
FIG. 1 is a block diagram of a urinary incontinence stimulator system embodying the invention.

FIG. 1 of the drawings shows in block diagram form a urinary incontinence stimulator system embodying the invention which includes a pulse generator 20, output circuitry 30 and enabling circuitry 50. The generator 20 provides series of pulses of varying duration and frequency. The output of the generator 20 is connected to output circuitry 30 which provides pulses of the same varying duration and frequency to an intra-anal electrode 40 for the time the circuitry 30 is enabled by recurring enabling signals supplied to it by the enabling circuitry 50.

The structure of a suitable intra-anal electrode for use in the system is well known and may, for example, be of the type described in U.S. Pat. No. 3,749,100 to H. A. von der Mosel or of the type used by Cardiac Recorders, Ltd.

Figure 2:
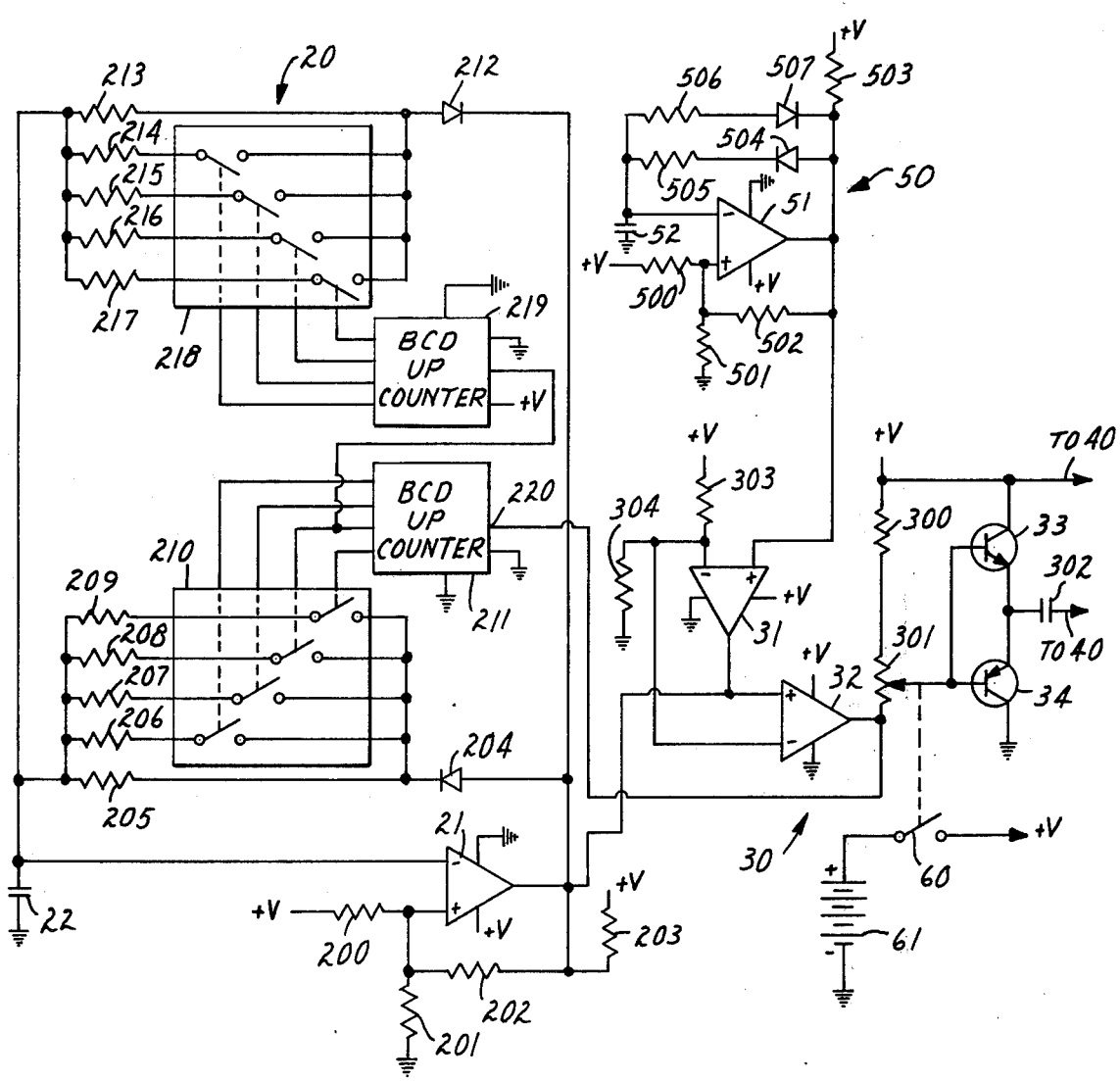
FIG. 2 is a schematic exemplary showing of circuit details for the circuit portions shown in block diagram form in FIG. 1.

Referring to FIG. 2, a detailed schematic is shown of exemplary circuits which are interconnected for providing the above-described functions for the pulse generator 20, the enabling circuitry 50 and the output circuitry 30.

The pulse generator 20 is essentially a free-running multivibrator and includes a comparator 21, the operation of which is controlled by the voltage on a capacitor 22 connected between ground and the negative input of the comparator. When the system is turned on by the operation of switch 60 to apply a D.C. voltage V+ from a battery 61 to the system, the voltage across capacitor 22 is low allowing the comparator 21, due to the bias presented by resistors 200, 201 and 202, to present a high signal at its output. A charging circuit for capacitor 22 is provided by resistor 203, diode 204 and resistor 205 connected in parallel with one or more of resistors 206–209, as determined by the switching provided by the semiconductor switching circuit 210. The switching circuit 210 is commercially available, and may, for example, be a type 4016 device, which is available from the RCA Corporation. The operation of the switching circuit 210 is controlled by the outputs of a binary coded decimal up counter 211 which changes with each input pulse supplied to the input 220 of counter 211. A type 4520 counter available from the RCA Corporation may be used to provide counter 211. The form of the source for providing input pulses to counter 211 is not critical and could, therefore, take on a number of forms. For convenience, the output of the output circuitry 30 is used to provide the input pulses to counter 211. Using the output of output circuitry 30, the counter 211 is connected to respond to the trailing edge of each pulse supplied to the counter 211. The resistor 206–209, have different values which are selected to provide 16 different charging rates which may be spaced in essentially equal increments over the range of charging rates provided. When capacitor 22 increases to about ⅔ of the voltage +V, the comparator 21 responds to provide a low signal at its output which allows the capacitor 22 to discharge via diode 212 and resistor 213 connected in parallel with one or more of resistors 214–217, as determined by the switching provided by semiconductor switching circuit 218 which may be the same as the switching circuit 211. When the voltage at capacitor 22 decreases to about ⅓ of the voltage V+, the comparator 21 again presents a high output. The operation of the switching circuit 218 is controlled by the outputs of a binary coded decimal up counter 219. The counter 219 may be provided by the same type of counter used for counter 211. An input for increasing the count of counter 219 is obtained from one of the outputs of the counter 211 with the counter 219 connected so as to respond to the leading edge of the output obtained from counter 211. The connection to an output of counter 211, for example, may be made so the counter 219 provides a different output to present a different discharge rate for capacitor 22 every fourth time the charge rate for capacitor 22 is changed by the output of counter 211. Sixteen different discharge rates, which may be spaced apart by essentially equal increments, are provided. In a circuit constructed in accordance with this invention, the values for capacitor 22 plus resistors 205–209 and 213–217 were selected causing the pulses presented at the output of the comparator 21 to have a duration which varied between about 0.5 milliseconds and 1.5 millseconds with a frequency which varied between about 10 and 55 Hz. With the signal generator 20 just described, pseudo random variable frequency and variable duration pulses are presented as an output from the comparator 21 and are applied to output circuit 30.

Whether pulses corresponding to those from generator 20 appear at the output of the circuit 30 is determined by enabling signals provided by the enabling circuit 50 connected to circuit 30. The enabling circuit 50 is also essentially a free-running multivibrator that is much like the multivibrator described for the pulse generator 20, except that its on-off times do not vary. The enabling circuit 50 includes a comparator 51, the operation of which is controlled by the voltage on the capacitor 52 connected between ground and the negative input of the comparator. When switch 60 is operated to provide the voltage V+ to the circuit 50, the capacitor 52 presents a low voltage allowing comparator 51, due to the bias presented by resistors 500, 501 and 502, to present a high signal at its output. A charging circuit for capacitor 52 is provided by resistor 503, diode 504 and resistor 505 allowing the voltage on capacitor 52 to increase after switch 60 is operated. When the voltage on capacitor 52 reaches about ⅔ of the voltage V+, the comparator 51 responds to provide a low signal at its output allowing the capacitor 52 to then discharge via resistor 506 and diode 507. When the voltage on capacitor 52 decreases to a level that is about ⅓ the voltage V+, the comparator 51 responds to again present a high signal at its output. The values of capacitor 52 and resistors 505 and 506 determine the duration for the high and low signals that are alternatively presented at the output of comparator 51. A high signal from comparator 51 enables the output circuitry 30 for the duration of such high signal so it can present a high signal to the load at the intra-anal electrode 40 when a high signal is presented to circuitry 30 from the pulse generator 20. The control of urinary incontinence provided by the system may deteriorate for some patients if the duration of the low signal from the enabling circuit 50 is too long. Suitable values for capacitor 52 and resistor 505 and 506 may be those which cause a high signal to be presented at the output of the output circuitry 30 for about the same time that a low signal is present with the maximum duration for the low signal being about two seconds.

A suitable output circuitry 30 includes two comparators 31 and 32 which are connected to the pulse generator 20 and the enabling circuit 50 to control the operation of two transmitters 33 and 34. The comparators 31 and 32, like comparators 21 and 51, may be of a type having a transistor at its output, the emitter of which is grounded with the collector providing the output for the comparator. The comparator presents a high signal when its output transistor is not conducting and presents a low when its output transistor is conducting.

A variable resistive path is presented between the voltage V+ and the output of comparator 32 by resistor 300 connected in series with a potentiometer 301. The transistor 33 is an NPN type which has its emitter connected to the emitter of a PNP type transistor 34. The collector of transistor 33 is connected to voltage V+ while the collector of transistor 34 is connected to ground. The base of each transistor is connected to the movable contact of potentiometer 301 so transistor 33 conducts when the output of comparator 32 is high, at which time transistor 34 is not conducting. When comparator 32 presents a low signal at its output, the conducting state for the transistors is reversed, i.e., transistor 34 is on and transistor 33 is off. A capacitor 302 is connected between one input to the intra-anal electrode 40 and the emitter electrodes of transistors 33 and 34. The other input of the electrode 40 is connected to the collector of transistor 33. Charging of capacitor 302 occurs whenver transistor 34 conducts to pass current through the load at electrode 40 in one direction. The level to which the capacitor 302 charges is determined by the setting of the potentiometer 301. When transistor 33 is turned on, the capacitor 302 is effectively connected across the load at electrode 40 to apply substantially the full voltage on the capacitor 302 across the load at the electrode 40. This current flow through the load is opposite in direction to the charging current. The switch 60 is ganged to the movable connector of potentiometer 301 so that the magnitude of the pulses provided to load at electrode 40 will be at a low level when switch 60 is moved to the on position by the user.

The negative inputs of comparators 31 and 32 are biased by series connected resistors 303 and 304 which connect between voltage V+ and ground. The negative input of comparators 31 and 32 is connected to the common connection of resistors 303 and 304. A common connection is provided for the outputs of comparators 21 and 31 plus the positive input of comparator 32. A high output will be presented at the output of comparator 31 when the output of the enabling circuit 50 is high. A high signal is presented to the comparator 32 only when the output of the pulse generator 20 and the output of comparator 31 are both high. Accordingly, the pulses from pulse generator 20 will be passed by the comparator 32 only for such times as the enabling circuit 50 presents a high signal to the comparator 31. With this arrangement, the user receives periods of bursts of pseudo random variable frequency and variable duration pulses spaced by a rest period of about equal duration when no pulses are received. The rest period is provided when the output of the enabling circuit 50 is low.

In the light of the above teachings, alternative arrangements and techniques embodying the invention will be suggested to those skilled in the art. The scope of protection afforded the invention is not intended to be limited to the specific embodiments disclosed, but is to be determined only in accordance with the appended claims.

What is claimed is:

1. A urinary incontinence stimulator system having an intra-anal electrode including:
   a generator means for providing a series of pulses of a duration and frequency which vary in a psuedo-random fashion;
   an enabling means for providing a recurring enabling signal; and
   an output circuit means connected to receive said pulses from said generator means and said enabling signal from said enabling means for enabling said output circuit for a time determined by said enabling signal for providing a series of pulses to the intra-anal electrode of the system in response to said pulses received from said generating means during said time.

2. A urinary incontinence stimulator system according to claim 1 wherein the time duration between successive enabling signals is of about the same time duration as one of said enabling signals.

3. A urinary incontinence stimulator system according to claim 1 wherein the time duration between successive enabling signals is less than about two seconds.

4. A urinary incontinence stimulator system according to claim 1 wherein the duration of the pulses in said series of pulses provided by said generator means varies between about 0.5 millisecond and 1.5 milliseconds.

5. A urinary incontinence stimulator system according to claim 1 wherein the frequency of the pulses in said series of pulses provided by said generator means varies from about 10 Hertz to 55 Hertz.

6. A urinary incontinence stimulator system according to claim 1 wherein said output circuit means includes a user adjustable means for varying the amplitude of said pulses to the intra-anal electrode.

7. A urinary incontinence stimulator system according to claim 1 wherein said generator means includes a comparator; a capacitor connected to said comparator for controlling the output of said comparator; a charging circuit connected between said capacitor and the output of said comparator for charging said capacitor when the output of said comparator provides a high signal; a discharging circuit connected between said capacitor and said comparator for discharging said capacitor when the output of said comparator provides a low signal; said charging circuit including means responsive to pulse inputs for changing the charging rate provided by said charging circuit; and said discharging circuit including means responsive to pulse inputs for changing the discharging rate provided by said discharging circuit.

8. A urinary incontinence stimulator system according to claim 1 wherein said output circuit means includes a first transistor; a second transistor; a capacitor; said first transistor connected in series with said capacitor across the intra-anal electrode, said second transistor connected in series with said capacitor and the intra-anal electrode for providing a charging circuit for said capacitor when said second transistor conducts; said first transistor conducting only when said enabling signal is provided and a pulse in said series of pulses provided by aid generator means is present and said second transistor conducting when said first transistor is not conducting.

9. A urinary incontinence stimulator system according to claim 8 wherein said output circuit means includes a user adjustable means connected to said second transistor for varying the level to which said capacitor can be charged.

* * * * *